United States Patent [19]
Hall et al.

[11] 3,963,660
[45] June 15, 1976

[54] PYRIDINE DIOXAMIC ACIDS AND ESTERS
[75] Inventors: Charles M. Hall; Herbert G. Johnson, both of Kalamazoo, Mich.
[73] Assignee: The Upjohn Company, Kalamazoo, Mich.
[22] Filed: Mar. 31, 1975
[21] Appl. No.: 563,919

Related U.S. Application Data
[63] Continuation-in-part of Ser. No. 403,677, Oct. 4, 1973, abandoned.

[52] U.S. Cl. ............... 260/295 R; 260/295.5 R; 424/263
[51] Int. Cl.² ............... C07D 213/55
[58] Field of Search ............... 260/295 R, 295.5 R, 260/295 AM, 295.5 A

[56] References Cited
UNITED STATES PATENTS

| | | | |
|---|---|---|---|
| 3,511,804 | 5/1970 | Duennenberger | 424/365 |
| 3,639,249 | 2/1972 | Luethi | 260/397.6 |

Primary Examiner—Norman A. Drezin
Attorney, Agent, or Firm—Martin B. Barancik; Roman Saliwanchik

[57] ABSTRACT
Novel compounds of formula I

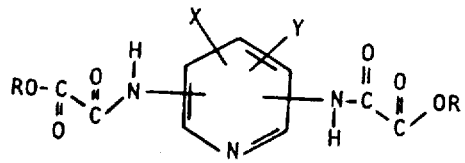

and

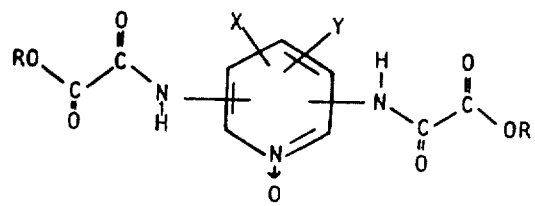

(1)

are useful in the prophylactic treatment of sensitized humans and animals for allergy and all anaphylactic reactions of a reagin or non-reagin mediated nature. The compounds are formulated with pharmaceutical carriers for oral, parenteral, inhalation or rectal means of administration.

35 Claims, No Drawings

PYRIDINE DIOXAMIC ACIDS AND ESTERS

CROSS REFERENCE TO RELATED APPLICATIONS

This application is a continuation-in-part application of our co-pending application Ser. No. 403,677, filed on Oct. 4, 1973 now abandoned.

BRIEF SUMMARY OF THE INVENTION

It has now been discovered that novel compounds of Formula I are useful in the prophylactic treatment of sensitized humans and animals for allergy and all anaphylactic reactions of a reagin or non-reagin mediated nature. The compounds are formulated with pharmaceutical carriers for oral, parenteral, inhalation or rectal means of administration.

DETAILED DESCRIPTION OF THE INVENTION

In accordance with this invention there are provided compounds represented by Formula I, and hereafter referred to as Group A:

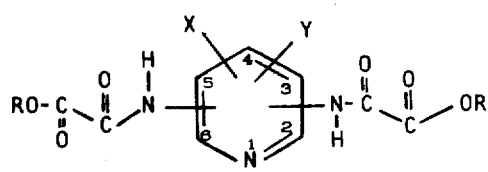

and

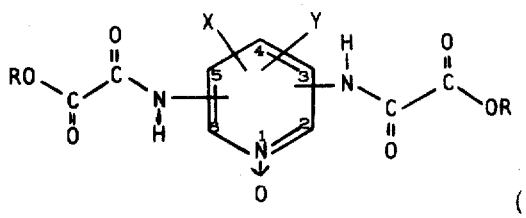

(I)

wherein each

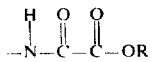

is located anywhere on the carbon ring with the proviso that one group cannot be ortho to the other group;

R is selected from the group consisting of hydrogen, alkyl from one through six carbon atoms, phenyl, and a pharmaceutically acceptable metal or amine cation;

X and Y can be the same or different and are selected from the group consisting of hydrogen, alkyl from one through four carbon atoms, phenyl, alkoxy from one through three carbon atoms, nitro, amino, trifluoromethyl, halogen, cyano and

wherein D is selected from the group consisting of hydrogen, alkyl from one through six carbon atoms and a pharmaceutically acceptable metal or amine cation with the proviso that when R is hydrogen or a pharmaceutically acceptable metal or amine cation, then D is the same as R, and R is alkyl from one through six carbon atoms or phenyl, then D is alkyl from one through six carbon atoms, phenyl or hydrogen; and pharmaceutically acceptable acid addition salts thereof.

A preferred group of compounds, hereafter referred to as Group B, are where R is selected from the group consisting of hydrogen, alkyl of from one through four carbon atoms, and a pharmaceutically acceptable metal or amine cation;

X and Y are the same of different and are selected from the group consisting of hydrogen, alkyl of from one through four carbon atoms, phenyl, alkoxy of from one through three carbon atoms, nitro, trifluoromethyl, halogen, cyano, and

wherein D is defined as in Group A, with the proviso that when D is alkyl, the upper carbon number limitation is four.

A more preferred group of compounds, hereinafter referred to as Group C, are compounds wherein the

groups are located at the 2 and 6 positions or the 3 and 5 positions;

R is selected from the group consisting of hydrogen and a pharmaceutically acceptable metal or amine cation.

X and Y are as defined in Group B.

A still more preferred group of compounds, hereinafter referred to as Group D, are compounds wherein the location of

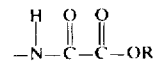

and R are as defined as in Group C, X is hydrogen and Y is selected from the group consisting of hydrogen, alkyl of from one through four carbon atoms, alkoxy of from one through three carbon atoms, nitro, trifluoromethyl, halogen, cyano, and

wherein D is defined as in Group B.

A further group of compounds, hereinafter referred to as Group E, are compounds wherein the location of

R, X and Y are defined as in Group D with the proviso that Y is limited to the 4 position.

A still further group of compounds, hereinafter referred to as Group F, are compounds wherein R, X and Y are defined as in Group E and the location of the

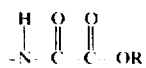

groups are at the 2 and 6 positions.

A further group of compounds hereinafter referred to as Group G are compounds wherein the location of the

group, R, X and Y are defined as in Group F with the proviso that halogen is fluoro, chloro, and bromo.

A still further group of compounds are compounds of successive Groups D, E, F and G, with the proviso that the nucleus to which the

and the X and Y groups are attached is

and its pharmaceutically acceptable acid addition salts.

As employed in the above disclosure and throughout the specification, the term "halogen" includes fluoro, chloro, bromo, and iodo. The term "alkyl" includes methyl, ethyl, propyl and isopropyl when limited to three carbon atoms, n-butyl and isomers thereof when limited to four carbon atoms, n-pentyl and n-hexyl and isomers thereof when limited to six carbon atoms. The term "pharmaceutically acceptable metal" includes alkali metals such as sodium and potassium, alkaline earth metals such as calcium and magnesium and other acceptable metals such as aluminum. The term "amine cation" includes all pharmaceutically acceptable cations from amines such as ammonia, tris-(hydroxymethyl)-aminomethane (THAM), D-threo-2-amino-1p-nitrophenyl-1,3-propanediol, N,N-bis(hydroxyethyl)-piperazine, 2-amino-2-methyl-1-propanol, 2-amino-2-methyl-1,3-propanediol and 2,2-bis(hydroxymethyl)-2,2',2''-nitrolotriethanol and further amines including $H_2NR'$, $HNR'_2$, and $NR'_3$, wherein R' is selected from the group consisting of alkyl from one to three carbon atoms, inclusive, and $-CH_2CH_2OH$.

Pharmaceutically acceptable acid addition salts refer to the salts which can be prepared at the nitrogen of the pyridine ring. Illustrative of these salts are hydrochloric, hydrobromic, hydriodic, nitric, sulfuric, oxalic, cyclohexanesulfamic salicylic, and the like.

The compounds of this invention can be prepared by methods known to the art. The appropriately substituted diaminopyridines (II) are suitable starting materials. These compounds are reacted with an alkyl oxalyl halide, preferably ethyl oxalyl chloride (IIIa), in a suitable solvent and base to form the dioxamate (IV). An alternative method of preparing the dioxamate is to react (II) with a dialkyl oxalate, preferably diethyl oxalate (IIIb) in neat solution or with an additional solvent, if necessary, at a temperature ranging from about 25°C. to about reflux temperature of the system.

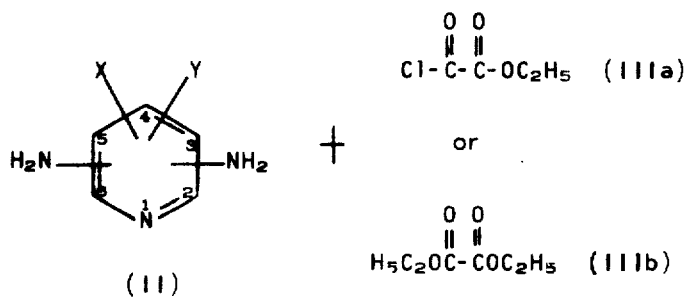

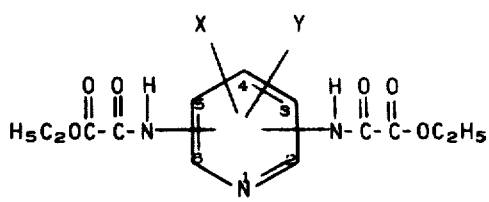

At this point of the synthetic pathway, the oxamate can be transesterified to other esters and/or converted to the diacid by hydrolysis and thence to the metal or amine salts by standard methods.

The N-oxide derivative of the pyridylyl dioxamic acid ester or salt can be readily prepared by oxidation of the diester with an oxidizing agent, such as m-chloroperoxybenzoid acid.

The appropriately X and Y substituted diaminopyridine starting materials are prepared by conventional substitution means well known in the art. These means depend somewhat upon the substituent itself, the placement of the substituent and the placement of the oxamic group.

The particular

substituents can be prepared by converting the corresponding diamino or dinitro pyridinecarboxylic acid, for example, to the ester, amide, etc., by standard methods. This can be done prior to the preparation of the dioxamate from the substituted diamino starting material.

Illustrative examples of starting materials of Formula II are below.

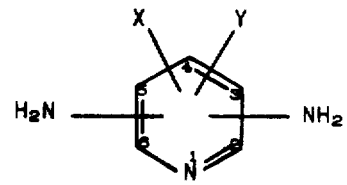

(II)

An additional route of preparing the starting materials, (II), for example, is by reacting a substituted dihalopyridine, for example, dichloropyridine (V) with ammonia under pressure and elevated temperature to produce the substituted diaminopyridine starting material (II)

TABLE I

| 2,6-diamino | | 2,4-diamino | | 2,5-diamino | | 3,5-diamino | |
|---|---|---|---|---|---|---|---|
| X | Y | X | Y | X | Y | X | Y |
| 4-BuO | H | 3-NO₂ | H | 3-CO₂H | H | 2-OBu | H |
| 4-EtO | H | 5-NO₂ | H | 3-Cl | H | 2-Cl | H |
| 4-MeO | H | 3-NO₂ | 6-C₃H₇ | 3-C₆H₅ | H | 2-OEt | H |
| 3-NO₂ | H | 6-Br | H | 3-CN | H | 2-OMe | H |
| 3-NO | H | 6-Br | 3-CN | 3-CF₃ | H | 2-O-Pr | H |
| 4-Cl | H | 6-Cl | 3-CN | 3-CH₃ | H | 4-C₆H₅ | H |
| 3-I | 5-I | 6-F | 3-CN | 3-nBu | H | 4-CN | H |
| | | 6-I | 3-CN | 3-Et | H | 4-CF₃ | H |
| 4-Et | H | 6-C₆H₅ | H | 3-Pr | H | 4-CH₃ | H |
| 4-i-pentyl-oxy | H | 6-CN | H | 3-NO₂ | H | 4-nBu | H |
| 4-CO₂H | H | 6-CF₃ | H | 4-CN | H | 4-Et | H |
| 3-CO₂H | 5-CO₂H | 6-CH₃ | H | 4-CF₃ | H | 4-Pr | H |
| 4-i-OC₃H₇ | H | 6-nBu | H | 4-NO₂ | H | 4-NO₂ | H |
| | | 6-Et | H | 6-CN | H | 4-CN | 2-Cl |
| 4-n-pentyl-oxy | H | 6-Pr | H | 6-CF₃ | H | 4-Et | 2-Cl |
| 3-phenyl | H | 6-NO₂ | H | 6-NO₂ | H | 4-CF₃ | 2-Et |
| 3-Br | H | 6-CN | 3-Cl | 3-CN | 6-H | 4-Pr | 2-Br |
| 3-MeO | H | 6-CF₃ | 3-Et | 6-Cl | 3-CN | 4-NO₂ | 2-OMe |
| 4-Br | H | 6-Pr | 3-Br | 3-CF₃ | 6-Cl | 4-Cl | 2-Et |
| 3-OEt | 5-OEt | 6-NO₂ | 3-OMe | 3-Cl | 6-CF₃ | 4-Et | 2-CF₃ |
| 3-CN | 5-CN | 6-CH₃ | 5-Cl | 3-OMe | 6-Et | 4-Br | 2-Pr |
| 4-C₆H₅ | H | 6-OEt | 5-CF₃ | 3-COOH | 6-Br | 4-OMe | 2-NO₂ |
| 4-CN | H | 5-Cl | 3-CN | 3-iPr | 4-iPr | 2-OMe | 6-OMe |
| 4-CF₃ | H | 5-CN | 3-Cl | 3-CN | 4-CN | 2-CH₃ | 6-OEt |
| 4-CH₃ | H | 5-Cl | 3-COOH | 3-Et | 4-Cl | 2-Cl | 6-Cl |
| 4-nBu | H | 5-COOH | 3-Cl | 3-Cl | 4-Et | 2-CF₃ | 6-Cl |
| 4-Et | H | 5-Me | 3-CF₃ | 3-OEt | 4-COOH | 2-CN | 6-Cl |
| 4-iPr | H | 5-OEt | 3-NO₂ | | | 2-OPr | 6-COOH |
| 4-NO₂ | H | 5-Et | 3-iOPr | | | 2-COOH | 6-COOH |
| 4-CN | 3-Cl | | | | | | |
| 4-CF₃ | 3-Et | | | | | | |
| 4-Pr | 3-Br | | | | | | |
| 4-NO₂ | 3-OMe | | | | | | |
| 3-CH₃ | 5-Cl | | | | | | |
| 3-OEt | 5-CF₃ | | | | | | |
| 4-Cl | 3-CN | | | | | | |
| 4-CN | 3-Cl | | | | | | |
| 4-Cl | 3-COOH | | | | | | |
| 3-COOH | 4-Cl | | | | | | |
| 4-Me | 3-CF₃ | | | | | | |
| 4-OEt | 3-NO₂ | | | | | | |
| 4-Et | 3-iOPr | | | | | | |

Once starting material II is prepared, it is reacted with an alkyl oxalyl halide or dialkyl oxalate. When using an alkyl oxalyl halide, reaction is carried out in base and solvent at standard conditions. Examples of suitable solvents are dimethylformamide (DMF), dioxane, and tetrahydrofuran. Appropriate bases include triethylamine, N-methylmorpholine, dimethylpiperazine, and N-methylpiperidine. When the dialkyl oxalate is employed, the starting material II of its substituted analogue is heated together with the dialkyl oxalate or an additional solvent such as a xylene or diphenyl ether if desired, thereby forming the dioxamate. The temperature is from about 25°C. to the reflux temperature of the system, preferably temperature between about 100°C. and reflux temperature of the system.

The dioxamate is then readily converted to the dioxamic acid by using dilute base such as sodium hydroxide, potassium hydroxide or potassium carbonate at temperatures ranging from about 25° to about 100°C., followed by addition of acid. The alkaline metal salts of the oxamate may be soluble in aqueous medium or relatively insoluble. If soluble in aqueous medium, the pH is adjusted with acid and the resulting precipitate is collected. If the alkaline metal salt is insoluble in aqueous medium, the precipitate per se can be collected and then heated in aqueous acid to an appropriate temperature, collecting the mixture, and isolating the desired diacid. The acid can then be easily converted to the metal or amine salt by contacting the diacid with two equivalents of the desired amine or metal hydroxide and heating in a sufficient amount of water to effect solubilization. The crystalline salts can be precipitated by the addition of an organic solvent, for example, methanol.

TABLE II

An illustrative list of compounds of this invention are the dioxamic acids prepared from the starting materials of Table I by methods of this application, and can be considered as being made and stated under the title "Table II".

TABLE III

The dioxamic acids of Table II are converted to pharmaceutically acceptable salts, e.g., metal and amine cations, and particularly the tris(hydroxymethyl)methylammonium salt by standard methods.

TABLE IV

The dioxamic acids of Table II are converted into compounds where R is alkyl of from one through six carbon atoms and phenyl by standard methods.

TABLE V

The compounds of Table IV are converted to pyridyl N-oxide oxamates by standard means.

TABLE VI

The compounds of Table V are converted to pyridyl N-oxide dioxamic acids by standard means.

TABLE VIII

The dioxamic acids of Table VI are converted to pharmaceutically acceptable salts, e.g., metal and amine cations, and particularly the tris(hydroxymethyl)methylammonium salt by standard methods.

Tables II through VIII are not rendered in the same manner as Table I for the purpose of brevity. However, the same scoping is intended.

The following examples are compounds in accordance with this invention. The compounds are intended not to limit but merely to exemplify the invention.

EXAMPLE 1

Pyridine-2,6-diyldioxamic acid a. Diethyl N,N'-2,6-pyridinediyldioxamate 2,6-Diaminopyridine (13.6 g.) is dissolved in 100 ml. of anhydrous DMF containing triethylamine (21 g.). The stirred reaction mixture is cooled to ice bath temperature and treated dropwise with ethyl oxalylchloride (30 g.). Stirring is continued for eighteen hours at room temperature, then the reaction mixture is poured into 1 l. of water. The product is collected by filtration, washed with water and dried under reduced pressure at 60°. Recrystallization from acetone gives a material melting at 179°–180° (15.0 g.).

b. Product

The diethyl ester (13.0 g.) is stirred at room temperature in 1 M sodium hydroxide (250 ml.) for one hour. The solution is acidified with 3M HCl to give the desired acid as a white solid. The product is collected by filtration, washed with water and dried at reduced pressure at 60°. (7.3 g.), m.p. >310°.

IR (Nujol): 3190, 1720, 1650, 1625, 1575, 735.

EXAMPLE 2

Pyridine-2,5-diyldioxamic acid a. 2,5-Diaminopyridine

A mixture of 2-amino-5-nitropyridine (10 g., 0.071 mole), 5% palladium on charcoal (1.0 g.), and methanol (200 ml.) is treated with hydrogen (40 psi) on a Parr hydrogenator until hydrogen uptake stops. The catalyst is removed by filtration and the solvent removed to leave a dark red oil which crystallizes upon standing.

b. Diethyl N,N'-2,5-pyridinediyldioxamate

To a mixture of the diamine prepared above, triethylamine (14 g., 0.14 mole), and anhydrous dimethylformamide (125 ml.), ethyl oxalyl chloride (18.4 g., 0.14 mole) is added slowly. The reaction mixture is stirred overnight at room temperature and then poured into water. The resulting solid is collected, treated with Darco and recrystallized from methanol to give a light red solid (5.68 g., 26%, m.p. 178°–180°). A small sample is recrystallized.

c. Product

Diethyl N,N'-2,5-pyridinediyldioxamate (1.0 g., 0.0032 mole) is stirred in 1.0N sodium hydroxide (25 ml.) at 70°–85° until solution is complete. The reaction mixture is diluted with water (25 ml.) and acidified (pH=3) with concentrated hydrochloric acid. The desired product is collected by filtration (0.35 g., 43%, m.p. 290°–295° dec.).

Analysis: nmr ($D_2O$ with THAM): 5.95δ (d, IH, 3-proton, $J_{3,4}$=8cps); 6.95δ (m, IH, 4-proton, $J_{4,3}$=8cps, $J_{4,6}$=2cps); 7.35δ (d, IH, 6-proton, $J_{6,4}$=2cps). IR(-Nujol) 3500, 3130, 2650 (broad), 1700, 1610, 1580, 1200 and others.

EXAMPLE 3

Disodio 2,6-dimethoxy-3,5-pyridinediyldioxamate a. Diethyl N,N'-(2,6-dimethoxy-3,5-pyridinediyl)dioxamate

Ethyl oxalyl chloride (5.71 g., 0.0418 moles) is added slowly with stirring at 0° to a solution of 3,5-diamino-2,6-dimethoxypyridine dihydrochloride (5.0 g., 0.027 moles) in DMF (50 ml.) and triethylamine (8.3 g., 0.0828 moles). The reaction mixture is stirred for one hour at 0°, then eighteen hours at room temperature. Dilution with water (500 ml.) gives a dark product that is collected by filtration, washed with water and dried. (3.8 g., m.p. 170°–173°). Recrystallizaton from ethanol and treatment with Darco gives a light green product. (1.9 g., m.p. 173°–174.5°, 25% yield).

Analysis: Calcd. for $C_{15}H_{19}O_8N_3$: C, 48.78; H, 5.19; N, 11.38. Found: C, 49.06; H, 5.18; N, 11.36. uv (EtOH) λ max (ε); 222 (10,300), 316 (14,600). IR (Nujol): NH 3390, = CH 3120, C=O 1730, 1710, C=C/C=N/amide II 1610, 1535, 1515, CH/C—O/-C—N/ether 1475, 1405, 1365, C=O/C—N/ether 1290, 1230, 1175, 1115, 1020, 1000. Mass. Spec.: Mol. ion 338 b. Product 1.75 g., (0.0048 moles) is stirred at room temperature in 1.0N NaOH (25 ml.). The sodium salt precipitates out as an off-white mass and is filtered and dissolved in water (400 ml.). The solution is acidified with 3N HCl (pH=4) and filtered. The filtrate is concentrated to 200 ml. under reduced pressure and the diacid disodium salt precipitates out as a white solid (.75 g., m.p. >310°).

Analysis Calcd. for $C_{11}H_9N_3O_8Na_2$: C. 36.99; H, 2.54; N, 11.76; Na, 12.88. Found: C, 37.53; H, 2.54; N, 12.05, Na, 11.95. uv ($H_2O$) λ max (ε): 210 sh (11,600), 304 (9,400). IR (Nujol): NH/OH 3480, 3400, 3350, C=O/$CO_2$/— C=N/C=C 1685, 1610,1530 CH/C—O/-C—N 1395, 1345, 1220, 1015.

The compositions of the present invention are presented for administration to humans and animals in unit dosage forms, such as tablets, capsules, pills, powders, granules, sterile parenteral solutions or suspensions, eye drops, oral solutions or suspensions, and oil-inwater and water in oil emulsions containing suitable quantities of the compound of Formula I. The preferred method of administration is by inhalation into the lung by means of an aerosol liquid or powder for insufflation.

For oral administration, either solid or fluid unit dosage forms can be prepared. For preparing solid compositions such as tablets, the compound of FIG. 1 is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration, such as syrups, elixirs, and suspensions, can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound..

Additionally, a rectal suppository can be employed to deliver the active compound. This dosage form is of particular interest where the mammal cannot be treated conveniently by means of other dosage forms, such as orally or insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung and containing a compound of the invention which is water-soluble. For treatment of allergic conditions of the nose, as rhinitis, compositions adapted for contact with nasal linings are preferred.

Compositions for inhalation are of three basic types: 1) a powder mixture preferably micropulverized with particle size, preferably from about 1 to about 5 microns; 2) an aqueous solution to be sprayed with a nebulizer; and 3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed is one which has a boiling point below 65°F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron." Mixtures of the above-mentioned propellants may suitably be employed. Examples of these propellants are dichloromethane (Freon 12), dichlorotetrafluoroethane (Freon 114), trichloromonofluoromethane (Freon 11), dichloromonofluoromethane (Freon 21), monochlorodifluoromethane (Freon 22), trichlorotrifluoroethane (Freon 113), difluoroethane (Genetron 142-A) and monochlorotrifluoromethane (Freon 13).

The term "unit dosage form," as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

It should be understood that the compositions disclosed herein refer to the groups of compounds A through G and those groups wherein the structure is pyridine and its pharmaceutically acceptable acid addition salts, as well as species illustratively exemplified.

An effective but non-toxic quantity of the compound is employed in treatment. The dosage of the compound for treatment depends on the route of administration and the potency of the particular compound. A dosage schedule for humans of from about 0.05 to about 20 mg. of compound in a single dose, administered parenterally or by inhalation in the compositions of this invention, are effective for preventing allergy attacks. Preferably, the single dose is from about 0.2 to about 20 mg. of compound. The oral and rectal dose is from about 1 to about 60 mg. in a single dose. Preferably, the single dose is from about 3 to about 30 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual insufflates 0.5 mg. of the tris(hydroxymethyl)aminomethane salt of pyridine-2,6-diyl-dioxamic acid. Four hours later the individual insufflates 0.005 mg. of the same compound and every four to six hours continues this reduced dosage until effective allergy prophylaxis is not provided. At that point 0.5 mg. of the compound is then taken followed by the reduced dosage every four to six hours. The dosage schedule continues in this manner.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, autoimmune diseases, exercise induced asthma, stress induced asthma, systemic anaphylaxis, and bird fancier's disease.

It should be noted that in the examples below wherein the salt form is used, the weight of compounds refers only to the compound in its acid form.

EXAMPLE 4

A lot of 10,000 tablets, each containing 1 mg. of pyridine-2,6-diyldioxamic acid, is prepared from the following types and amounts of ingredients:

| | |
|---|---|
| Pyridine-2,6-diyldioxamic acid | 10 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 5 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, the compressed into tablets.

These tablets are useful in preventing hay fever attacks at a dose of 1 tablet every four to six hours.

EXAMPLE 5

One thousand two-piece hard gelatin capsules, each containing 20 mg. of pyridine-2,5-diyldioxamic acid, are prepared from the following types and amounts of ingredients:

| | |
|---|---|
| Pyridine-2,5-diyldioxamic acid | 20 Gm. |
| Lactose | 400 Gm. |
| Talc | 15 Gm. |
| Magnesium stearate | 1 Gm. |

The ingredients are mixed well and filled into capsules of the proper size.

Capsules so prepared are useful in preventing attacks of bronchial asthma at a dosa of one capsule every four to six hours.

EXAMPLE 6

One thousand tablets, each containing 4 mg. of 2,6-dimethoxypyridine-3,5-diyldioxamic acid, are prepared from the following types and amounts of ingredients:

| | |
|---|---|
| 2,6-Dimethoxypyridine-3,5-diyldioxamic acid | 4 Gm. |
| Microcrystalline cellulose NF | 410 Gm. |
| Starch | 100 Gm. |
| Magnesium stearate powder | 2 Gm. |

The ingredients are screened and blended together and pressed into 516 mg. tablets.

The tablets are useful to protect against food allergy at a dose of 1 tablet before meals.

EXAMPLE 7

A sterile preparation suitable for intramuscular injection and containing 0.1 mg. of pyridine-2,6-diyldioxamic acid in each milliliter is prepared from the following ingredients:

| | | |
|---|---|---|
| Pyridine-2,6-diyldioxamic acid | 0.1 | Gm. |
| Benzyl benzoate | 200 | ml. |
| Methylparaben | 1.5 | Gm. |
| Propylparaben | 0.5 | Gm. |
| Cottonseed oil q.s. | 1,000 | ml. |

One milliliter of this sterile preparation is injected for prophylactic treatment of allergic rhinitis.

EXAMPLE 8

Six hundred ml. of an aqueous solution containing 3 mg. of the tris(hydroxymethyl)aminomethane (THAM) salt of pyridine-2,6-diyldioxamic acid per ml. is prepared as follows:

| | | |
|---|---|---|
| Tris(hydroxymethyl)aminomethane (THAM) salt of pyridine-2,6-diyldioxamic acid | 1.8 | Gm. |
| Sodium chloride | 5 | Gm. |
| Water for injection q.s. | 600 | ml. |

The THAM salt and sodium chloride are dissolved in sufficient water to make 600 ml. and sterile filtered.

The solution is placed in nebulizers designed to deliver 0.25 ml. of solution per spray.

The solution is inhaled into the lungs every four to six hours for prevention of asthmatic attacks.

EXAMPLE 9

A powder mixture consisting of 0.2 gram of tris(hydroxymethyl)aminomethane salt of pyridine-2,6-diyldioxamic acid and sufficient lactose to make 5 grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 10

Twelve grams of an aerosol composition are prepared from the following ingredients:

| | |
|---|---|
| Tris(hydroxymethyl)aminoethane salt of pyridine-2,6-diyldioxamic acid | 0.10 Gm. |
| Freon 12 | 1.440 Gm. |
| Freon 114 | 2.160 Gm. |
| Water | 7.700 Gm. |
| Sorbitan monoleate | 0.600 Gm. |

The THAM salt is dissolved in the water and chilled to $-30°C$. and added to the chilled Freons. The twelve grams of composition are added to a 13 cc. plastic coated bottle and capped with a metering valve. The metering valve releases 80 mg. of composition in an aerosol. The aerosol is inhaled every four to six hours for prevention of asthmatic attacks.

EXAMPLE 11

In individuals who require continual treatment in the Examples 4 through 10, the dosage of the Example is given initially and each succeeding administration of the drug is at 1/50 of the initial dosage. This maintenance dosing is continued until effective allergy prophylaxis is not obtained. The initial dosage of Examples 4 through 10 is then started once more, followed by the maintenance dosages.

EXAMPLE 12

After allowing for the different solubilities of the compounds and the activity of the particular compound as measured, for example, by the in vivo rat passive cutaneous anaphylaxis assay, a suitable quantity of each of the compounds of Table II through Table VIII and Examples 1–3 and 14–15, is substituted for the active compound in the compositions and uses of the Examples 4 through 10. Results showing anti-allergy activity are obtained.

EXAMPLE 13

The rat passive cutaneous anaphylaxis assay is run in the following manner:

Female Sprague-Dawley 250 gm. rats are skinsensitized with rat anti-ovalbumin homocytotropic antibody that is heat labile and has a passive cutaneous anaphylaxis titer of 1:128. After a 72-hour latency period, the animals are challenged i.v. with 4 mg. oval-bumin (OA) + 5 mg. Evans blue dye and the test compound. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

The tris(hydroxymethyl)aminomethane salt of pyridine-2,6-diyldioxamic acid is prepared by dissolving the dicarboxylic acid in an equivalent weight of aqueous tris(hydroxymethyl)aminomethane and is tested in the rat passive cutaneous anaphylaxis assay in the above manner.

The inhibitory dose$_{50}$ for the tris(hydroxymethyl)-aminomethane salt of pyridine-2,6-diyldioxamic acid is 0.01 mg./kg.

TABLE VIII

The compounds of Tables II and IV are converted to pharmaceutically acceptable acid addition salts by conventional means.

A novel, preferred method for preparing the 4-substituted diamino pyridine starting materials follows. The buildup of the oxamic side chain is as previously disclosed. The synthesis is illustrated for the 2,6-diamino pyridine molecule but is applicable to other isomeric diamino pyridines.

1,4-Dihydro-4-oxo-pyridine-2,6-dicarboxylic acid is contacted with a halogenating agent such as phosphorous pentachloride or thionyl chloride in a lower alkanol solvent such as methanol, at standard conditions, thereby forming dimethyl 4-chloro-pyridine-2,6-dicarboxylate. The diester is then converted to the diamide with ammonia. At this point the 4-halo substituent can be converted to a different substituent, for example, the halo group of the substituted diamide can be replaced with an alkoxy group by reacting the halo substituted diamide with sodium alkoxide thereby forming the 4-alkoxy-substituted diamide. The 4-substituted diamide is then reduced with bromine in potassium hydroxide under standard conditions to produce the 4-substituted 2,6-diamino pyridine reactant.

The above illustrative reactants used in converting a carboxy group to an amino group are applicable to all member compounds of the invention.

When preparing 2,6-pyridyl dioxamic molecules where the 4-substituent is nitro or cyano, the starting materials are readily prepared by the following procedures. 2,6-Dimethylpyridine N-oxide is reacted with potassium cyanide in dimethyl sulfate at standard conditions forming 4-cyano-2,6-dimethylpyridine. This compound is then oxidized to the diacid with potassium permanganate.

The 4-nitro substituted starting material is prepared by contacting 2,6-dimethylpyridine N-oxide with nitric acid and sulfuric acid thereby forming the 2,6-dimethyl-4-nitropyridine. The N-oxide is reduced to the pyridine compound with phosphorous trichloride and then oxidized to the 4-nitropyridine 2,6-dicarboxylic acid with potassium permanganate.

Following are additional specific examples:

EXAMPLE 14

N,N'-[4-methoxy-2,6-pyridinediyl]dioxamic acid a. 2,6-biscarbomethoxy-4-chloropyridine A mixture of chelidamic acid, (31 g) phosphorous pentachloride (105 g) and carbon tetrachloride is refluxed until evolution of hydrogen chloride ceases. To the solution thus obtained is added methanol (150 ml.), dropwise under gentle reflux. The solution is refluxed for two hours and then the solvents removed by distillation. The residue is poured into about 500 ml of ice water and the solid collected by filtration. Recrystallization from methanol gives long white needles (21.1 g., m.p. 142°–143°, 54% yield).

b. 2,6-biscarboxamido-4-chloropyridine

Ammonia gas is passed into a stirred suspension of 2,6-biscarbomethoxy-4-chloropyridine (5.0 g) in methanol (150 ml.), with cooling. After about thirty minutes the mixture is stirred for one hour at room temperature. The addition of ammonia is stopped and stirring continued for one hour at room temperature. Filtration gives the product as a white crystalline solid (4.0 g., m.p. 323°–325°, (dec), 92% yield).

c. 2,6-biscarboxamido-4-methoxypyridine 2,6-biscarboxamido-4-chloropyridine (8.0 g) is suspended in methanol (700 ml) and sodium methylate (32 ml of 25% solution in methanol) added. The reaction mixture is refluxed for six hours with stirring. The solution is cooled and the product precipitated as a white solid. The product is collected by filtration, washed with water and dried (4.18 g., m.p. 292°–294° dec., 53.4% yield).

d. 2,6-diamino-4-methoxypyridine

To a solution of potassium hydroxide (15 g) in water (100 ml) at 0° is added bromine (2.75 ml) dropwise. To this solution is added all at once the above 2,6-biscarboxamido-4-methoxypyridine (5.0 g). After stirring for 1 ½ hours at 0° the resulting solution is heated rapidly to 75°–80° for twenty minutes. The reaction mixture is cooled to room temperature and acidified to pH 5 with glacial acetic acid and then made basic (pH 10) with 40% sodium hydroxide solution. The reaction mixture is filtered and the filtrate extracted with $CH_2Cl_2$ (10 × 100 ml) and the combined extracts dried with anhydrous sodium sulfate. Removal of the solvent leaves a light green solid (2.24 g). The solid is chromatographed on silica gel (200 g, 2250 ml., 5% MeOH in $CH_2Cl_2$, 750 ml 7.5% MeOH in $CH_2Cl_2$, 1050 ml. 10% MeOH in $CH_2Cl_2$) and 150 ml fractions collected. Fractions 10–27 are combined and the solvent removed to leave a pale green solid. Recrystallization from benzene gives pale green needles (1.15 g, m.p. 134°–135.5°, 32% yield).

Analysis Calc'd for $C_6H_9ON_3$: C, 51.79; H, 6.52; N, 30.20. Found: C, 52.17; H, 6.83; N, 29.83. u.v. (MeOH) λMax. (ε): 207 (33,050), 245 (6,950), 286 (7,500). IR (Nujol): NH 3440, 3340, 3180, NH def/C=N/C=C 1650, 1615, 1585, 1570, 1480, C—N/-C—O 1210, 1175. Mass Spec.: Mol. ion 139 e. Diethyl N,N'-[4-methoxy-2,6-pyridinediyl]-dioxamate

Ethyl oxalyl chloride (1.1 g) is added slowly at 0° to a solution of 2,6-diamino-4-chloropyridine (.5 g) in dimethylformamide (5 ml) and triethylamine (.9 g). The reaction mixture is stirred one hour at 0°, then eighteen hours at room temperature. Dilution with water (100 ml) gives a light yellow solid. The resulting solid is collected by filtration and recrystallized from methanol to give the desired product as white needles (.94 g, m.p. 155°–156.5°, 77% yield).

Analysis Calc'd. for $C_{14}H_{17}O_7N_3$: C, 49.55; H, 5.05; N, 12.38. Found: C, 49.51; H, 5.03; N, 12.18. u.v.

(MeOH) λMax. (ε): 248 (17,750), 291 (12,250). Mass Spec.: Mol. ion 339.

IR (Nujol): NH 3400, 3330, =CH 3140, C=O 1740, 1725, 1710, C=N/C=C/amide II 1615, 1590, 1550, 1515, C—N/C—O/other 1310, 1280, 1210, 1200, 1165, 1035, Arom CH 850.

f. N,N'-[4-methoxy-2,6-pyridinediyl]dioxamic acid

Diethyl N,N'-[4-methoxy-2,6-pyridinediyl]-dioxamate (.5 g) is stirred in aqueous 0.5 M sodium hydroxide solution (10 ml) for 4–5 minutes. The sodium salt precipitates out in a white mass and is filtered, dissolved in water (25 ml) and acidified with 3N HCl to pH 3 to give the desired diacid as a white solid (.13 g, m.p. 270° (dec.), 31% yield).

EXAMPLE 15

N,N'-[4-chloro-2,6-pyridinediyl]dioxamiac acid a. 2,6-diamino-4-chloropyridine

To a solution of potassium hydroxide in water (100 ml) at 0° is added bromine (2.75 ml) dropwise. To this solution is added all at once 2,6-biscarboxamido-4-chloropyridine (5.0 g). After stirring for two hours at 0° the resulting solution is warmed to room temperature and acidified to pH 5 with glacial acetic acid and then made basic (pH 10) with 40% sodium hydroxide solution. The reaction mixture is filtered and the filtrate extracted with $CH_2Cl_2$ (10 × 50 ml). The combined extracts are dried with sodium sulfate. Removal of the solvent leaves a tan solid (3.4 g). The solid is chromatographed on silica gel (300 g., 1.5 l., 2.5% MeOH in $CH_2Cl_2$) and 150 ml fractions collected. Fractions 8–20 are combined and the solvent removed to leave a tan solid. Recrystallization from benzene gives tan needles (2.15 g., m.p. 102°–103.5° 60% yield).

Analysis Calc'd for $C_5H_6N_3Cl$: C, 41.82; H, 4.21; N, 29.27; Cl, 24.70. Found: C, 41.32; H, 4.38; N, 29.30; u.v. (MeOH) λMax. (ε): 249 (10,950), 309 (11,550). Mass spec.: Mol. ion 143. IR (Nujol): NH/3440, 3420, 3340, 3170, C=N/C=C/NH def 1645, 1620, 1595, 1565, 1535, other 1440, C—N/other 1295, 1235, 1105, NH def/CH def 880, 805, 780.

b. Diethyl N,N'-[4-chloro-2,6-pyridinediyl]-dioxamate

Ethyl oxalyl chloride (4.0 g) is added slowly at 0° to a solution of 2,6-diamino-4-chloropyridine (2.0 g) in dimethylformamide (15 ml) and triethylamine (3.1 g). The reaction mixture is stirred one hour at 0°, then eighteen hours at room temperature. Dilution with cold water gives a light yellow solid. The resulting solid is collected by filtration and recrystallized from ethanol to give the desired product as white needles (3.25 g., m.p. 164°–166°, 67.8% yield).

Analysis Calc'd for $C_{13}H_{14}O_6N_3Cl$: C, 45.42; H, 4.11; N, 12.23; Cl, 10.32. Found: C, 45.07; H, 4.18; N, 11.98; Cl, 10.27. u.v. (MeOH) λMax. (ε): 217 (sl. sh.) (13,850), 243 (16,900), 300 (14,650). IR (Nujol): NH 3380, 3300, =CH 3120, C=O 1720, C=C/C=N amide II 1580, 1535, 1510, other 1430, C—O/C—N other 1300, 1265, 1205, 1155, 1030, γCH 855.

c. N,N'-[4-chloro-2,6-pyridinediyl]dioxamic acid

Dimethyl N,N'-[4-chloro-2,6-pyridinediyl]-dioxamate (1.0 g) is suspended in water (10 ml) and aqueous 1M sodium hydroxide (6 ml) added with stirring for 4–5 minutes at room temperature. The sodium salt precipitates out in a white mass and is filtered, dissolved in water (50 ml) and acidified with 3N HCl to pH 2 to give the desired diacid as a white solid (.15 g., m.p. >320°, 18% yield).

All temperatures of the preceding examples are in °C.

We claim:
1. A compound of the formula

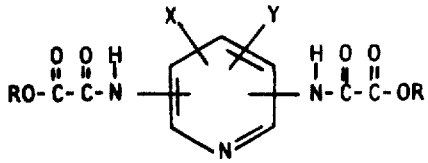

and

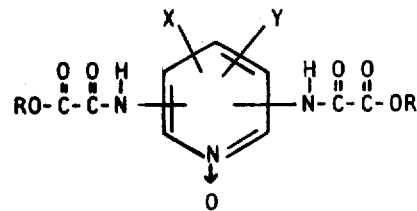

wherein each

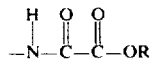

group is located anywhere on the carbon ring with the proviso that one group cannot be ortho to the other group;

R is selected from the group consisting of hydrogen, alkyl from one through six carbon atoms, phenyl, and a pharmaceutically acceptable metal or amine cation;

X and Y are the same or different and are selected from the group consisting of hydrogen, alkyl from one through four carbon atoms, phenyl, alkoxy from one through three carbon atoms, nitro, amino, trifluoromethyl, halogen, and

wherein D is selected from the group consisting of hydrogen and alkyl from one through six carbon atoms, and a pharmaceutically acceptable metal or amine cation with the proviso that when R is hydrogen or a pharmaceutically acceptable metal or amine cation, then D is the same as R and when R is alkyl from one through six carbon atoms or phenyl, then D is alkyl from one through six carbon atoms, phenyl or hydrogen;

and pharmaceutically acceptable acid addition salts thereof.

2. A compound in accordance with claim 1 wherein R is selected from the group consisting of hydrogen, alkyl of from one through four carbon atoms, and a pharmaceutically acceptable metal or amine cation;

X and Y are the same or different and are selected from the group consisting of hydrogen, alkyl from one through four carbon atoms, phenyl, alkoxy from one through three carbon atoms, nitro, trifluoromethyl, halogen, and

wherein when D is alkyl, the upper limit of carbon atoms is four.

3. A compound in accordance with claim 2 wherein the

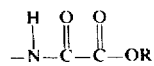

groups are located at the 2 and 6 positions or the 3 and 5 positions;

R is selected from the group consisting of hydrogen and a pharmaceutically acceptable metal or amine cation.

4. A compound in accordance with claim 3 wherein X is hydrogen and Y is selected from the group consisting of hydrogen, alkyl from one through four carbon atoms, alkoxy from one through three carbon atoms, nitro, trifluoromethyl, halogen, and

wherein D is the same as R.

5. A compound in accordance with claim 4 with the proviso that Y is located at the 4-position.

6. A compound in accordance with claim 5 wherein the

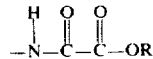

groups are located at the 2 and 6 positions.

7. A compound in accordance with claim 6 wherein halogen is selected from the group consisting of fluoro, chloro, and bromo.

8. A compound in accordance with claim 1 wherein the

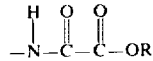

groups are at the 2 and 6 positions of

R is selected from the group consisting of hydrogen, alkyl of one to three carbon atoms, inclusive, and a pharmaceutically acceptable metal or amine cation and X and Y are hydrogen.

9. A compound in accordance with claim 1 wherein the

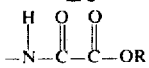

groups are at the 2 and 5 positions of

R is selected from the group consisting of hydrogen, alkyl from one to three carbon atoms, inclusive, and a pharmaceutically acceptable metal or amine cation and X and Y are hydrogen.

10. A compound in accordance with claim 1 wherein the

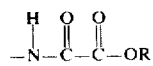

groups are at the 3 and 5 positions of

R is selected from the group consisting of hydrogen, alkyl from one to three carbon atoms, inclusive, and a pharmaceutically acceptable metal or amine cation;

X is 2-methoxy, Y is 6-methoxy.

11. A compound in accordance with claim 8 where R is selected from the group consisting of hydrogen and tris(hydroxymethyl)methylammonium.

12. A compound in accordance with claim 9 where R is selected from the group consisting of hydrogen and tris(hydroxymethyl)methylammonium.

13. A compound in accordance with claim 10 where R is selected from the group consisting of hydrogen and tris(hydroxymethyl)methylammonium.

14. A compound in accordance with claim 4 wherein the structure is

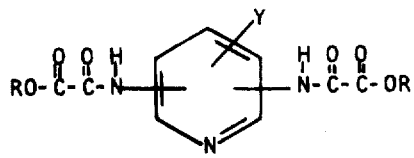

and its pharmaceutically acceptable acid addition salts.

15. A compound in accordance with claim 5 wherein the structure is

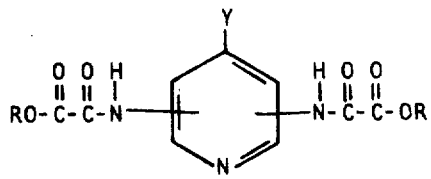

and its pharmaceutically acceptable acid addition salts.

16. A compound in accordance with claim 6 wherein the structure is

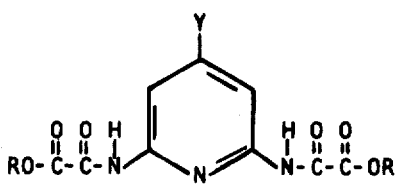

and its pharmaceutically acceptable acid addition salts.

17. A compound in accordance with claim 7 wherein the structure is

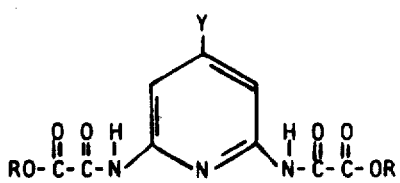

and its pharmaceutically acceptable acid addition salts.

18. A compound in accordance with claim 1 wherein the

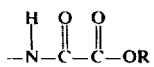

groups are located at the 2 and 6 positions.

19. A compound in accordance with claim 2 wherein the

groups are located at the 2 and 6 positions.

20. A compound in accordance with claim 3 wherein the

groups are located at the 2 and 6 positions.

21. A compound in accordance with claim 4 wherein the

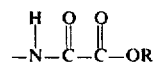

groups are located at the 2 and 6 positions.

22. A compound in accordance with claim 18 wherein X and Y are hydrogen.

23. A compound in accordance with claim 18 wherein X is hydrogen and Y is 4-chloro.

24. A compound in accordance with claim 18 wherein X is hydrogen and Y is 4-methoxy.

25. A compound in accordance with claim 1 wherein the

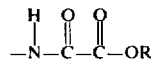

groups are located at the 2 and 5 position and X and Y are hydrogen.

26. A compound in accordance with claim 25 wherein R is hydrogen.

27. A compound in accordance with claim 22 wherein R is ethyl.

28. A compound in accordance with claim 22 wherein R is hydrogen.

29. A compound in accordance with claim 1 wherein the

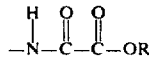

groups are at the 3 and 5 position and X and Y are at the 2 and 6 position and are methoxy.

30. A compound in accordance with claim 29 wherein R is ethyl.

31. A compound in accordance with claim 29 wherein R is hydrogen.

32. A compound in accordance with claim 23 wherein R is ethyl.

33. A compound in accordance with claim 23 wherein R is hydrogen.

34. A compound in accordance with claim 24 wherein R is ethyl.

35. A compound in accordance with claim 24 wherein R is hydrogen.

* * * * *